(12) United States Patent
Linjama et al.

(10) Patent No.: US 10,051,354 B2
(45) Date of Patent: Aug. 14, 2018

(54) APPARATUS FOR COMPREHENSIVE PERCEPTION OF SOUND

(71) Applicant: FLEXOUND SYSTEMS OY, Espoo (FI)

(72) Inventors: Jukka Linjama, Espoo (FI); Heikki Tuominen, Espoo (FI)

(73) Assignee: FLEXOUND SYSTEMS OY, Espoo (FI)

(*) Notice: Subject to any disclaimer, the term of this patent is extended or adjusted under 35 U.S.C. 154(b) by 0 days.

(21) Appl. No.: 15/032,712

(22) PCT Filed: Jan. 22, 2015

(86) PCT No.: PCT/FI2015/000003
§ 371 (c)(1),
(2) Date: Apr. 28, 2016

(87) PCT Pub. No.: WO2015/118217
PCT Pub. Date: Aug. 13, 2015

(65) Prior Publication Data
US 2016/0286291 A1    Sep. 29, 2016

(30) Foreign Application Priority Data

Jan. 24, 2014 (FI) .................................. 20140019

(51) Int. Cl.
*H04R 9/06* (2006.01)
*H04R 11/00* (2006.01)
(Continued)

(52) U.S. Cl.
CPC ............ *H04R 1/028* (2013.01); *A61M 21/00* (2013.01); *H04R 5/02* (2013.01); *H04R 7/045* (2013.01);
(Continued)

(58) Field of Classification Search
CPC ........ G10K 11/172; H01J 23/20; H04R 1/2819
(Continued)

(56) References Cited

U.S. PATENT DOCUMENTS 4,064,376 A * 12/1977 Yamada ............. A61H 23/0218
297/217.4
4,357,499 A * 11/1982 Bruel .................... E04B 1/8218
367/13
(Continued)

FOREIGN PATENT DOCUMENTS

CN   1183882 A   6/1998
CN   1402624 A   3/2003
(Continued)

OTHER PUBLICATIONS

International Search Report, dated May 12, 2015, from corresponding PCT Applicataion.
(Continued)

*Primary Examiner* — George C Monikang
(74) *Attorney, Agent, or Firm* — Young & Thompson

(57) ABSTRACT

An apparatus for comprehensive perception of sound, preferably a cushion, where vibration and sound is produced with a mechanical device wrapped inside a padding, wherein
(a) the device radiates sound by generating mechanical vibration directly to the padding that can be felt and listened on the outer surface of the padding,
(b) the device radiates airborne sound through the padding,
(c) in order to avoid acoustical and mechanical resonances, the padding includes an acoustically denser and lossy layer and a layer that is acoustically less dense and porous, and
(d) the device includes at least one board, and the vibration of the boards is generated using at least one vibrating mechanical actuator.

10 Claims, 7 Drawing Sheets

(51) Int. Cl.
*H04R 1/02* (2006.01)
*A61M 21/00* (2006.01)
*H04R 5/02* (2006.01)
*H04R 7/04* (2006.01)
*H04R 1/28* (2006.01)

(52) U.S. Cl.
CPC ............... *A61M 2021/0022* (2013.01); *A61M 2021/0027* (2013.01); *H04R 1/025* (2013.01); *H04R 1/288* (2013.01); *H04R 1/2811* (2013.01); *H04R 2201/023* (2013.01); *H04R 2201/029* (2013.01); *H04R 2400/03* (2013.01)

(58) Field of Classification Search
USPC .................. 381/87, 332–336, 354, 162, 191
See application file for complete search history.

(56) References Cited

U.S. PATENT DOCUMENTS

| | | | |
|---|---|---|---|
| 4,782,533 | A | 11/1988 | Haynie |
| 5,512,715 | A | 4/1996 | Takewa et al. |
| 2007/0025574 | A1 | 2/2007 | Azima et al. |
| 2007/0253591 | A1 | 11/2007 | Popilek et al. |
| 2008/0263749 | A1* | 10/2008 | Leong .................. A61F 11/14 2/209 |
| 2009/0010468 | A1 | 1/2009 | Oser et al. |
| 2012/0039057 | A1 | 2/2012 | Paleczny et al. |
| 2013/0228392 | A1 | 9/2013 | Iwata et al. |

FOREIGN PATENT DOCUMENTS

| | | |
|---|---|---|
| CN | 1655645 A | 8/2005 |
| CN | 202161073 U | 3/2012 |
| CN | 202739471 U | 2/2013 |
| CN | 202981271 U | 6/2013 |
| CN | 103349467 A | 10/2013 |
| DE | 10 2011 015 747 A1 | 10/2012 |
| EP | 1 947 901 A1 | 7/2008 |
| EP | 2 690 888 A2 | 1/2014 |
| FR | 2 900 881 A1 | 11/2007 |
| JP | 2004-57261 A | 2/2004 |
| JP | 5190150 B1 | 4/2013 |
| WO | 2006/034125 A2 | 3/2006 |

OTHER PUBLICATIONS

Finnish Search Report, dated Sep. 23, 2014, from corresponding Finnish Application.
Supplementary European Search Report issued in Application No. EP 15 74 6365, dated Jun. 19, 2017.
Aug. 8, 2017, CN communication issued for related CN application No. 2015800025177.

* cited by examiner

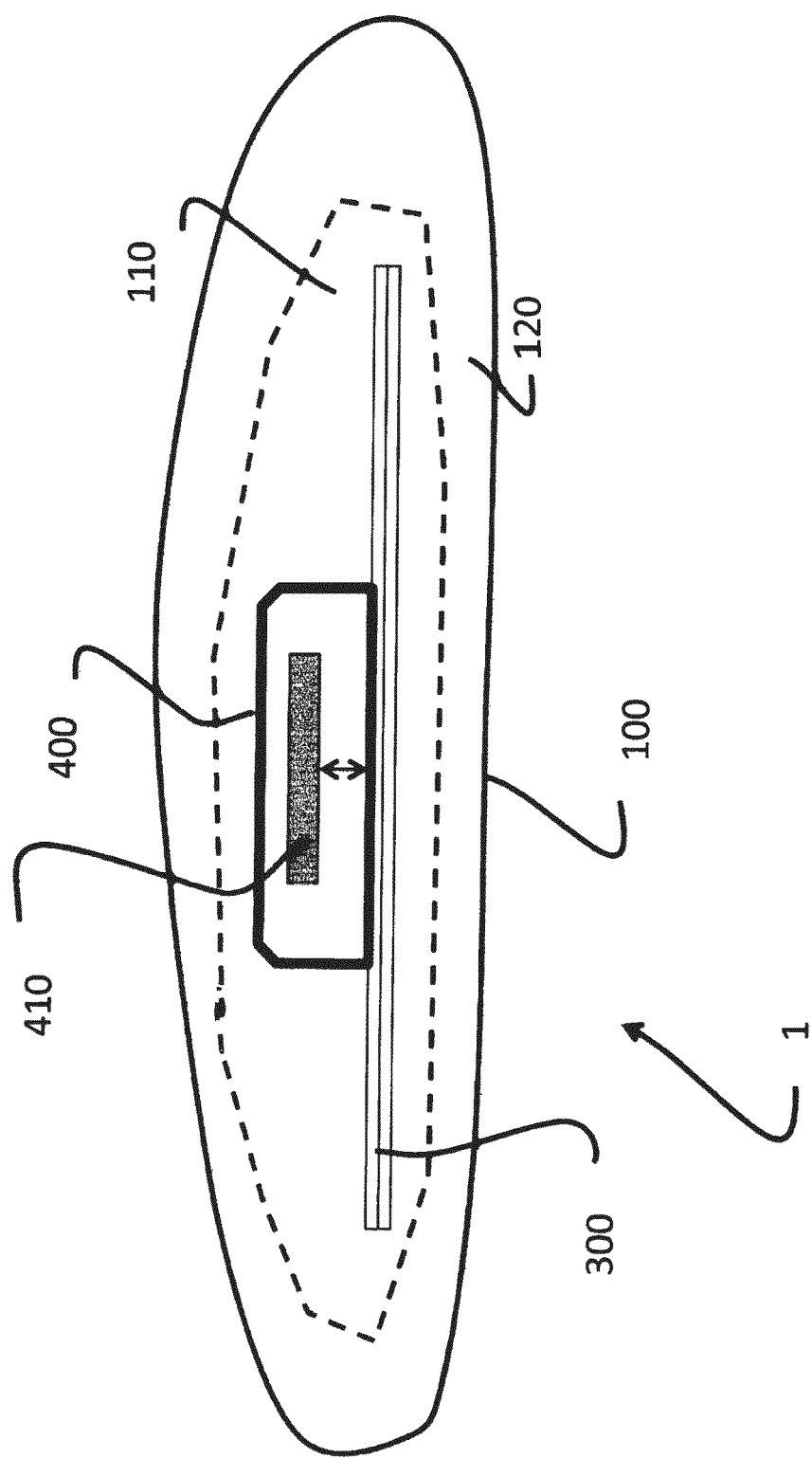

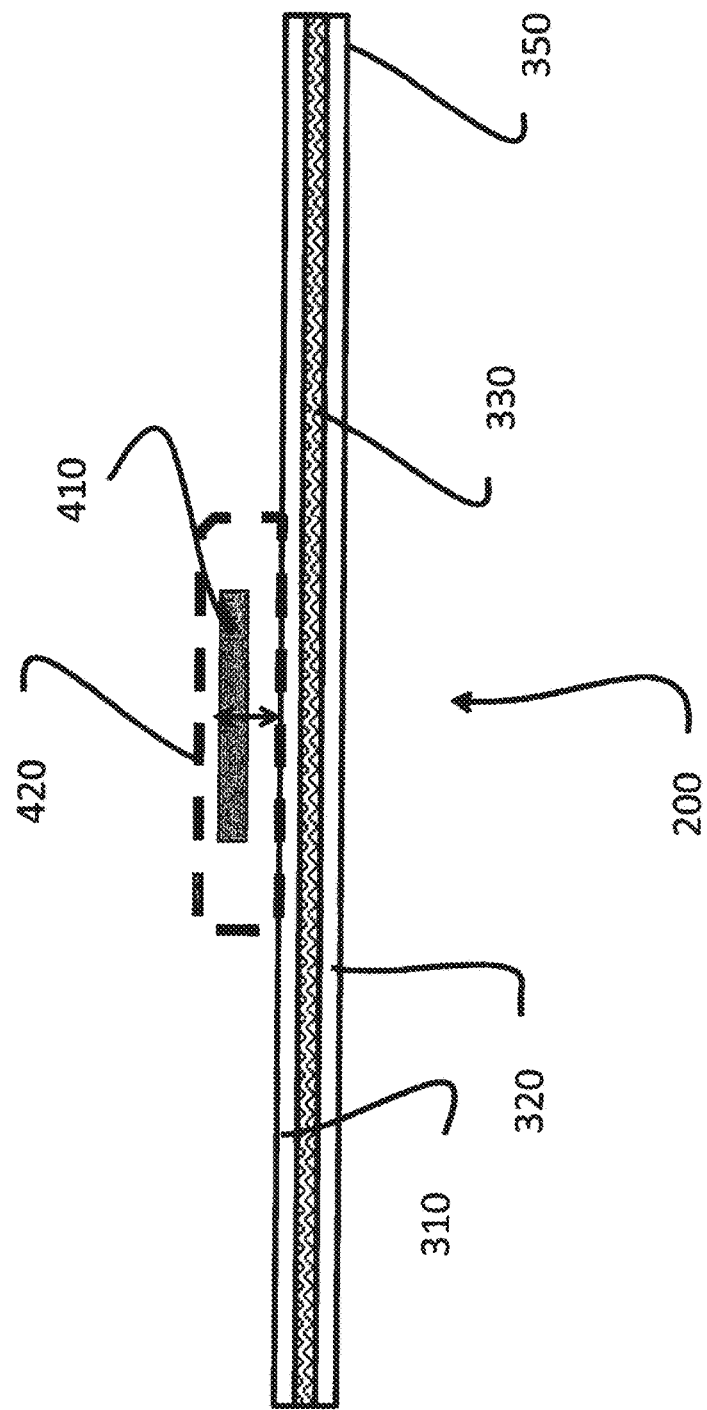

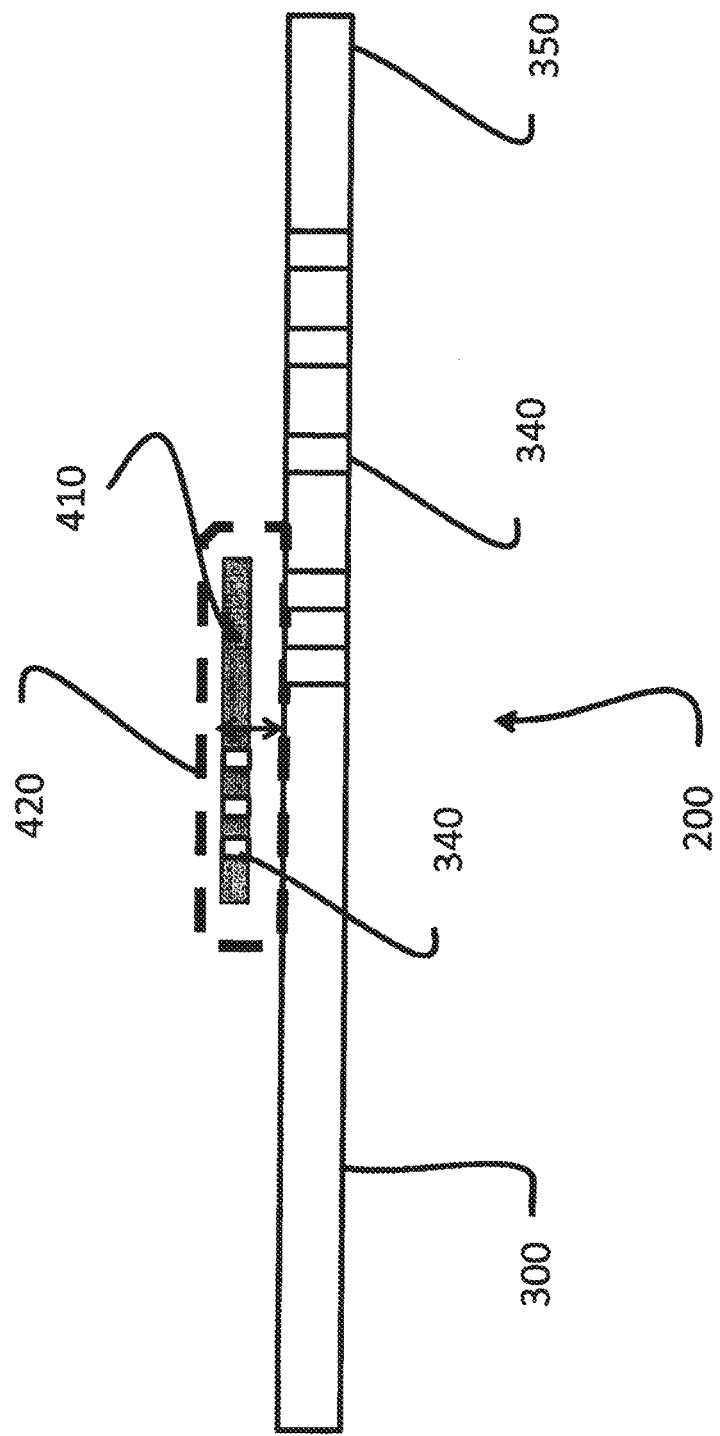

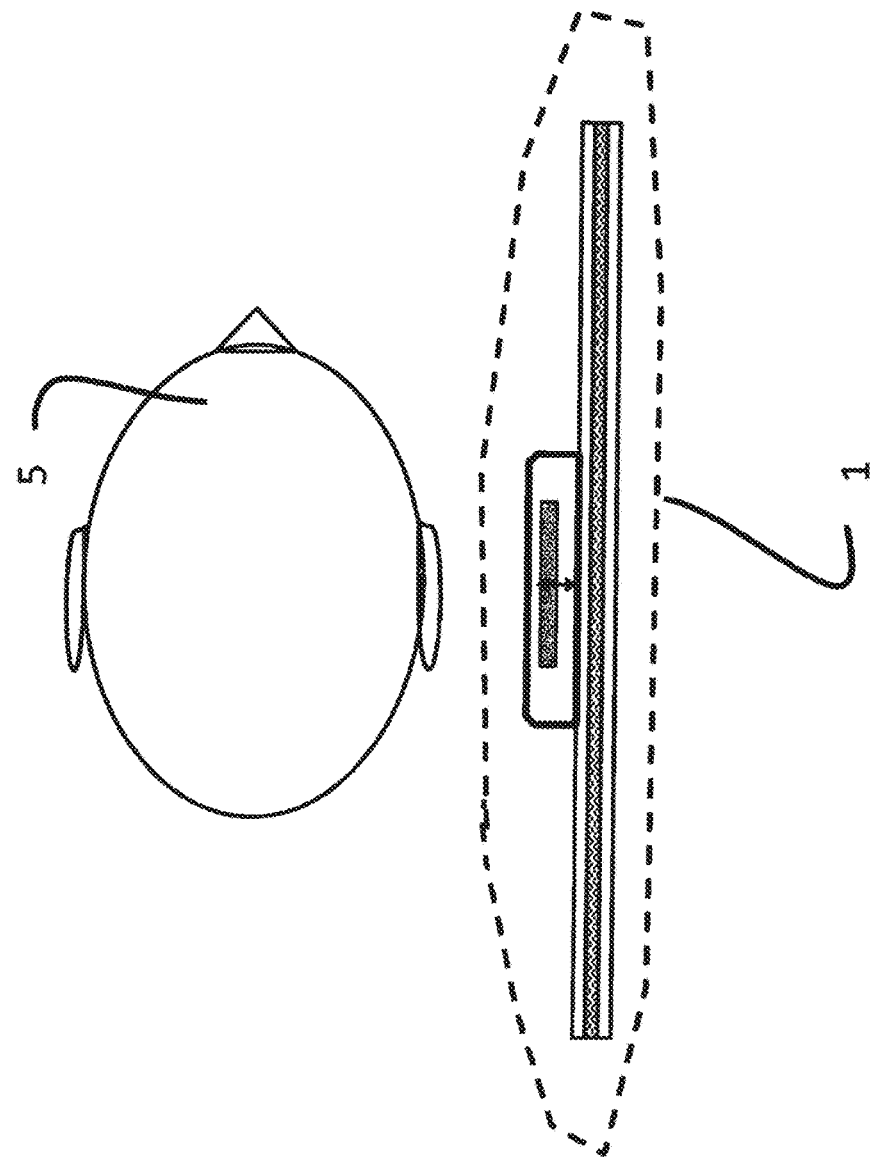

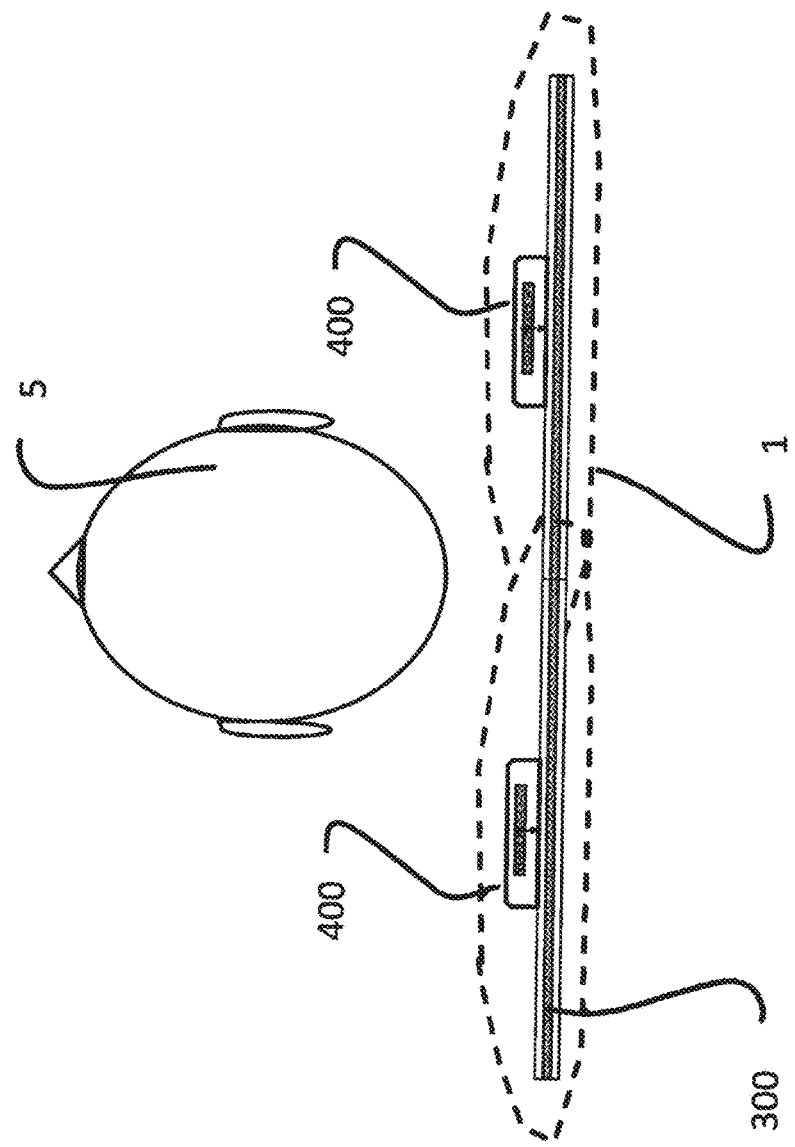

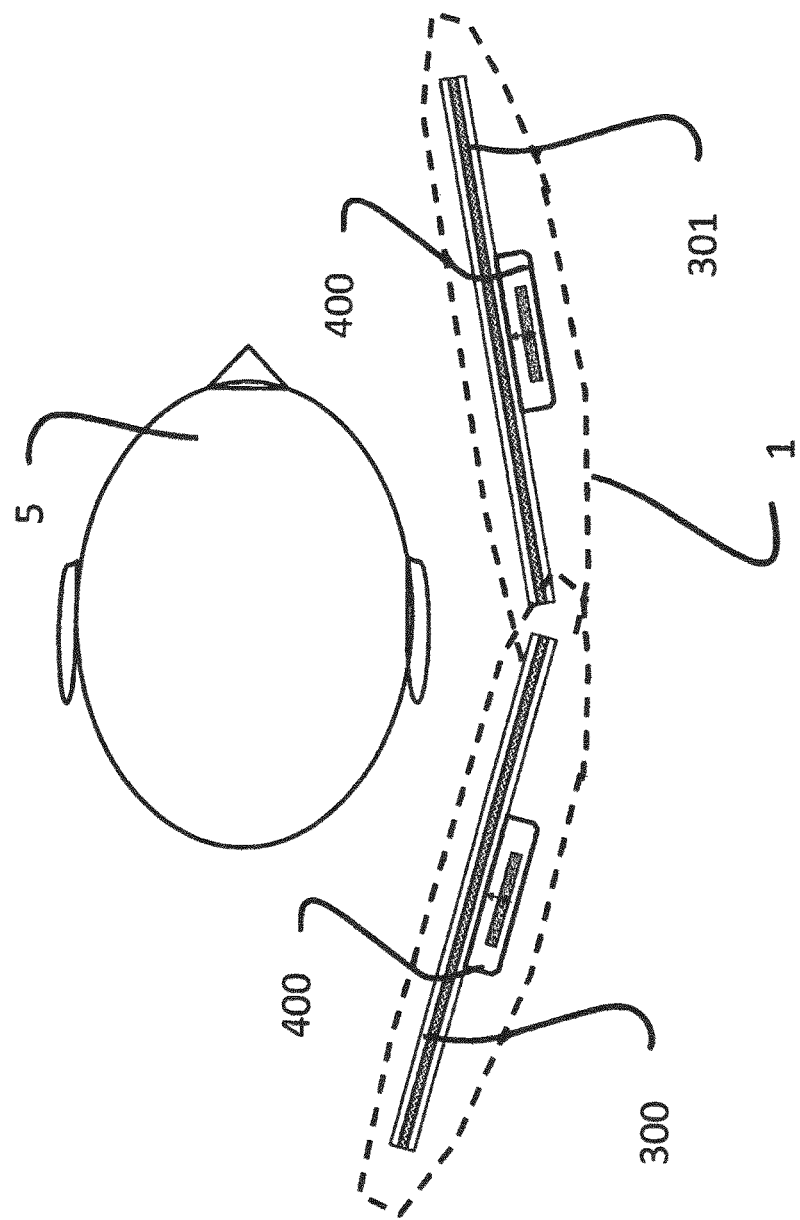

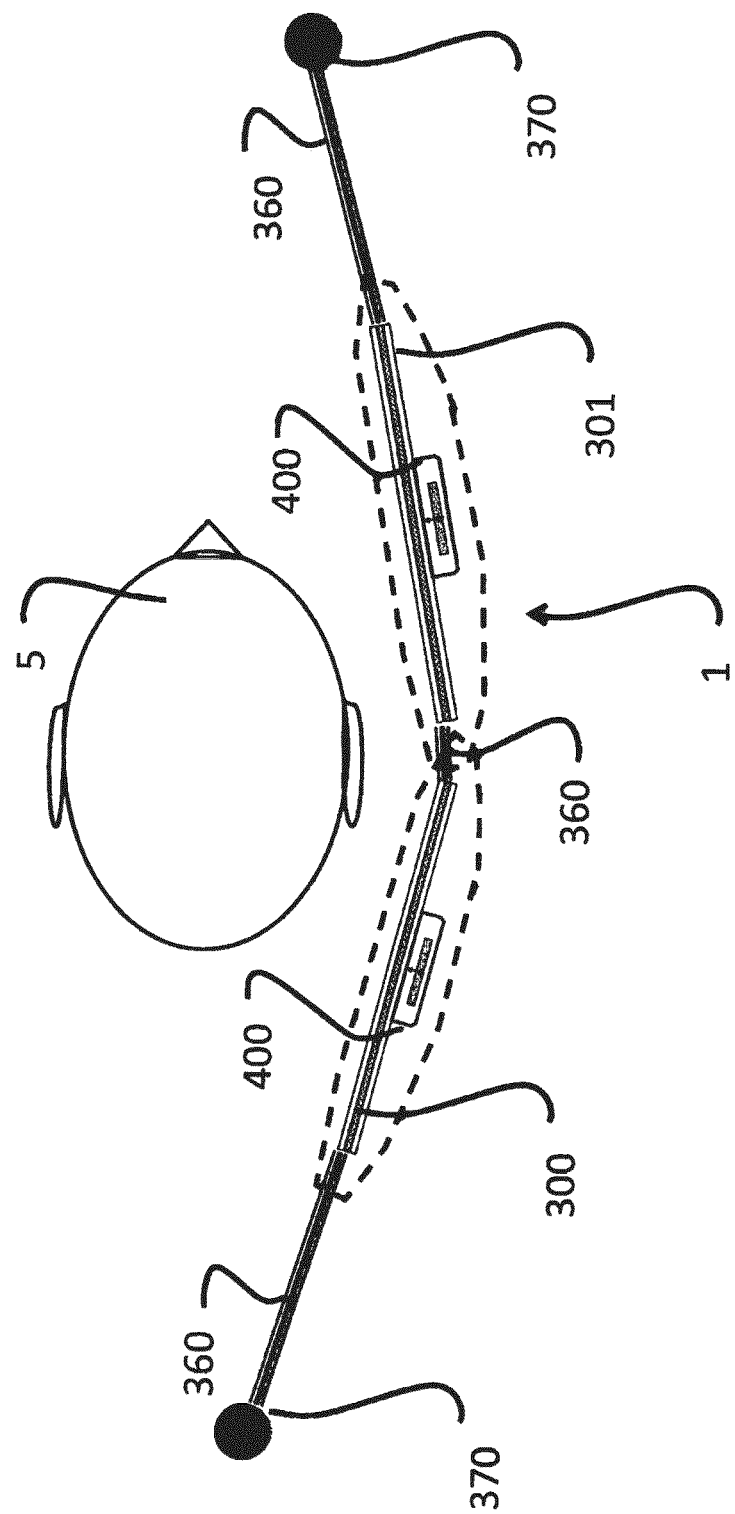

APPARATUS FOR COMPREHENSIVE PERCEPTION OF SOUND

FIELD OF THE INVENTION

The invention is about an apparatus for listening to music and sound content using both hearing and sense of touch. The solution of the invention, haptic cushion, offers an immersive listening experience at a level comparable to headset listening, together with tactile sensation.

BACKGROUND FOR THE INVENTION

Besides hearing, the perception of sound is also based on the sense of touch. Sense of touch is mostly a subconscious sense working in the background, giving essential information on the condition of the body (e.g. pain sensation) and directing motoric action (skin sense tells you when you have a good grip of the object you're holding). When listening, the attention is directed to the sound coming to the ears through air, or airborne sound. However, almost always sound also causes some mechanical vibration in the proximity of the listener, for example in the seat, clothes or directly on skin. This sound, structure-borne sound that is felt as tactile sensation, makes the listening experience more intimate and deeper. The vibration is especially felt with low frequency sounds. Also sounds somewhat higher than in the bass frequencies are perceivable. The sense of touch of the skin is typically most sensitive in the frequency range of 50-300 Hertz, and in some parts of skin vibration is perceivable up to almost 1000 Hz. Through the sense of touch—haptically—also the hearing-impaired can perceive sound information, for example speech.

For the existing sound reproduction systems with current technology, it's typical that listening is possible either from a distance (loudspeakers) or close to the device (headset). Current prior art technology does not offer loudspeakers for listening both from a distance and through ear contact.

There exist small loudspeakers that are used for close up listening, for example those used in a pillow. There are, however, limitations to this kind of prior art solutions that are based on airborne sound radiation; a) the sound is sharpest right next to the loudspeaker elements, b) the sound is spatially localized to loudspeaker element locations, and c) there is no proper bass reproduction.

It is well-known that powerful low frequency loudspeakers (subwoofers) or specific mechanical vibrators in, for example, the seat or the headset, can be used to add tactile sensation to the listening experience.

Thus, with prior art solutions, the skin sensation complementing the listening experience is typically produced by solutions that are separate from the listening device itself.

The following four publications represent prior art technology. The Japanese publication JP2004057261 presents a pillow with a loudspeaker in it. Besides the loudspeaker, the pillow also contains padding. The loudspeaker includes parts that touch the user's neck when they rest their head on the pillow. In the United States patent application US20130228392, the loudspeaker is surrounded by a waterproof layer of polymeric foam. Besides being waterproof, the layer enhances sound producing vibrations. In the US patent application US20120039057, the padding is meant to electrically insulate a piezoelectric board. A German publication DE102011015747 presents a plate meant for a wall-mount loudspeaker. The board contains foam of a ceramic material, and the board is partly lined.

THE INVENTION IN SUMMARY

One objective of the invention is excellent sound reproduction and tactile sensation, when one or more sources of sound are placed inside a cushion or some other padded product, while the cushion or the padded product is, in its normal use, meant to be in direct contact with the user. In other words, the sound source, or parts of it, touches the user indirectly, through the padding—the first part of the sound produced by the sound source is sound coming through the air, and the other part is sound experienced haptically through sense of touch. In one embodiment of the invention, the cushion or the padding needs to be of a specific kind for the sounds to be of high quality, so that especially the low sounds have a high quality and the user feels the vibration of the cushion with their head, neck and/or other part of the body. In the application, the padding is referred to as wrapping.

The objective of the invention is to avoid the limitations and flaws existing in the sound reproduction systems of prior art technology: it is possible to listen to music in various situations, and to enjoy the immersive experience brought by the tactile sensation, as well. Especially, it is possible to have a good listening experience very close to the sound source, even with direct ear contact. This is why the invention enables a well-balanced listening experience without spreading disruptive, powerful bass sounds all around. Also, it is beneficial that hearing will remain receptive to any sounds from the surroundings.

Prior art technology offers seat shaking effect vibrators and separate bass loudspeakers (subwoofers) for, for example, cars or home cinemas. The invented device produces, in a smaller scale, both the effect vibration and the bass reproduction. Adding the tactile sensation to it also entails feelings of being hugged, which for everyone is pleasant, and to some special groups, essential. The low sounds conveyed through the tactile sensation also produce a massage-like relaxing experience.

The invention includes a vibrating apparatus (board) and its wrapping. Their objective is to convey sound and vibration with good efficiency and balance, for the user to both hear and feel via surface contact.

The board has a sound source, preferably a mechanical actuator, which makes it vibrate. The actuator can be any mechanical vibrator or deformation-generating part with a wide enough operating frequency range. The board has to be sufficiently rigid, so that during close up listening, distributes the sound source to be audible in a larger area than the loudspeaker element alone would allow. Further, it is beneficial for the board to be mechanically adequately damped (have energy dissipation or losses). Mechanical losses in the board enable the following beneficial features: a) there are no sharp resonances distorting the frequency response, and that b) the vibration caused by the actuator does not consist of standing waves alone but also of propagating waves with spatial phase differences.

The padding has to
  be broader than the board, thus distributing the sound further and adding sense of space during close up listening
  be mechanically lossy, hence adding the mechanical losses or damping of the board
  be acoustically lossy, hence damping the acoustic resonances between the head and the board be adequately flexible on the surface and adequately transparent acoustically.

These preferable properties of the padding help to avoid, in direct surface contact with the ear, formation of mechanical or acoustic resonances that may deteriorate the perceived sound quality. Further, these preferable properties of the board and padding help to achieve a condition of vibroacoustic impedance matching between the device and the head, and thus enable a good overall efficiency for acoustic energy transmission from the haptic cushion to the ear.

LIST OF FIGURES

Next, the invention is explained in more detail referring to the following Figures.

FIG. 1: Haptic cushion structured according to the invention.

FIG. 2: Implementation of one embodiment of the invention.

FIG. 3: Implementation of an alternative embodiment of the invention.

FIG. 4: Device in use, listening to monophonic sound content.

FIG. 5: Listening to stereophonic sound content and its uses.

FIG. 6: Embodiment with flexible structure.

FIG. 7: Embodiment with extension of the device using material, mesh or membrane.

INVENTION IN DETAIL

Some preferable embodiments of the invention are presented in the FIGS. 1-7. The presented embodiments serve as examples, and even if the text describing a particular embodiment may refer to another embodiment, it is usually only referring to one possible option. Features of different embodiments can be combined and thus create new embodiments.

FIG. 1 is an embodiment of a haptic cushion (1), based on enclosed inertial mass actuator. The device (200) consists of an actuator (400) and a board (300). The actuator (400) produces vibrating force between a flexibly hung inertial mass (410) and the board (300), causing the board (300) to vibrate. The vibration emits sound by causing both mechanical vibration directly on the wrapping (100), which can be felt and heard on the surface of the wrapping, and as sound coming via air through the wrapping (100).

The vibration of the board (300) emits mechanical energy in two ways. Firstly, it makes the wrapping (100) vibrate, directing vibration energy to the surface of the wrapping. Secondly, it emits sound coming via air through the wrapping (100). Each of the mechanisms works together resulting in vibration on the surface, felt by the sense of touch and sound coming through air, audible with ears. Therefore, vibration energy is transmitted as a balanced combination of structure-borne and airborne sound to the listener.

One way to implement the actuator (400) is to use a loudspeaker element with its cone mechanically attached to the board (300), causing the rest of the mass of the loudspeaker element to function as inertial mass (410). The board (300) can also be made to vibrate with other kinds of actuators, including solutions where an external vibrating force is directed mechanically to the board (300), and solutions that create internal mechanical deformations to the board (300).

There is a bending wave field forming on the board (300), advancing from the actuator (400) towards the edge of the board and partly reflecting back from the edge. The reflections may cause sharp mechanical resonances which may affect negatively to the perceived acoustic and haptic frequency response. Reflections may cause distinct resonance peaks to the frequency response in the frequency band 20-1000 Hz. To avoid those unwanted resonances, it is useful to include lossy properties to the device (200) and wrapping (100).

Mechanical losses can be caused with, for example, directly with lossy material choices for the board (300), or by different constructions. Constructions may be local stiffness and damping concentrations in the board (300), or composite parts that dissipate energy e g where the lowest vibration modes have deformation. For instance, the deformation in the contact between the actuator (400) and board (300) can be utilized as a localized damping arrangement.

One type of lossy construction is to utilize the lossy damping features of the wrapping (100) attached to the board (300). The wrapping may contain natural fibers, artificial fibers or both. The wrapping may contain, for example, cotton, viscose or foam plastic.

The wrapping (100) may consist of two or more acoustically different layers. One preferable embodiment uses an interior layer (110) that is porous but rather dense and massive, and an exterior layer (120) that has a low flow resistance and transmits airborne sound well. Layered structure can be also a gradual distribution of porous materials, having different flow resistances and densities. A preferable arrangement provides an impedance matching, where the (complex) radiation impedance of the board (300) is gradually changing inside padding (100) and approaching the value 400 Pa s/m, the characteristic acoustic impedance of air in free field. Examples of dense, porous layers with high flow resistance are dense foam plastic or felt. Examples of layers that transmit sound well and have low flow resistance are cotton wool, wool or light weight fabric.

FIG. 2 presents one embodiment of the device. The device (200) consists of an acoustically open actuator (420) and a lossy construction (350) consisting of a two layer board (310 and 320) with an elastic layer (330) in between for adding loss. The elastic layer may be, for example, a two-sided tape, a glued membrane or viscoelastic glue. The board consists of, for example, wood, plastic or metal. The elastic layer can attach to each other two boards of the same material, or two boards made of different materials. Acrylic board, metallic laminates or plywood are examples of usable board materials. Boards (310 and 320) may be of any shape, including flat or curved plane surfaces, and may have corrugated profile and/or non-isotropic stiffness properties.

As an alternative for the enclosed actuator (400) presented in FIG. 1, one can also use an acoustically open actuator (420) presented in FIG. 2. Then the motion of the actuator's inertial mass (410) also emits locally more sound through the air. Although the wrapping mutes direct sound coming through the air, in this embodiment it can also be utilized and make the other side of the haptic cushion more loudspeaker-like, a side that can be better audible further away.

FIG. 3 presents an alternative embodiment of the device (200), where the lossy construction (350) contains one perforated board. The perforation (340) causes the following useful features:

together with the wrapping's acoustic losses they bring useful damping to the structure and they reduce, especially with close up listening, sharp localization of the sound near the actuator (410), since they mute with acoustic short-circuit the more powerful sound emittance in the middle of the board The small perforations on the board (the preferred hole diameter being less than 4 mm) cause damping due to viscosity of air, and due to flow resistance of the padding (100). Perforations bigger than this can be used as well. Larges holes provide a way to regulate the frequency response and sound localization, if needed. Perforations can be used in the board (300) or in the inertial mass (410) or in both. One use of perforation is micro-perforation, using very small holes that approach porous material behaviour.

Another use of perforation in the soft padding is to allow adaptive behavior of the material due to compression: For instance, when the user's head is lying on the haptic pillow, the compression of the padding causes some of the perforation to become partially closed. Furthermore, perforation can be used to add acoustical transparency (reduce flow resistance) to otherwise tight and dense wrapping materials.

Further, another alternative use of perforation might be holes or pipes through the device that have extended length dimension. For instance, holes having length in the range of 10-40 mm that act as pipe resonators (or Helmholtz resonators) for amplitude and/or phase regulation of the acoustical or haptic frequency response.

In addition to using perforation that utilizes small holes, perforation elements can have complex shape (like f-holes on the violin sound board). This perforation arrangement may be used for instance for adjusting mechanical vibration mode shapes, or for adjusting spatial properties of sound radiation from the board.

FIG. 4 presents one use for the haptic cushion, where the head (5) of the listener rests on the cushion (1) and feels the vibration of the wrapping's surface. The sound quality is good, since the ear rests on a padding (120) that is flexible and that breathable (has low flow resistance), and for the ear the situation is close to sensing sound in a free field. Also, the perceived sound is not localized at the actuator, but it can be heard and felt evenly in different parts of the board. These aspects combined enable an experience that feels natural.

The use presented in FIG. 4 can also be done so that the other ear or both ears are in contact to the surface of the cushion (1) without losing practically any perceived quality of sound.

In the embodiment of FIG. 5 the same board (300) has at least two actuators (400) combined, which enables the formation of a feeling of space with stereophonic sound or multichannel sound content.

The embodiment of FIG. 6 uses its own board (300 and 301) for each of the actuators, making it possible to bend it, for example, to a headrest.

In the embodiment of FIG. 7 the boards (300) and (301) have been attached to a larger fabric, mesh or membrane (360), that can be used as a supporting element from the suspension parts (370) and that also expands the acoustic area of the board.

The invention claimed is:

1. An apparatus for comprehensive perception of sound, comprising:
    padding comprising at least two acoustically different layers including an interior layer and an exterior layer,
    the interior layer being a porous layer,
    the exterior layer being a lossy layer,
    the interior layer being acoustically denser than the exterior layer,
    the interior and exterior layers of the padding reducing acoustical and mechanical resonances;
    a mechanical device enclosed inside the padding with all sides of the mechanical device being covered by both the interior layer and the exterior layer of padding,
    the mechanical device producing vibration and sound,
    the mechanical device comprising at least one board and at least one vibrating mechanical actuator,
    wherein the at least one vibrating mechanical actuator causes vibration of the at least one board, the vibration of the at least one board emitting sound, the sound having a first sound part and a second sound part, wherein,
    (a) the mechanical device radiates the first sound part by generating mechanical vibration directly to the padding, wherein the first sound part can be felt and listened on an outer surface of the padding, and
    (b) the mechanical device radiates the second part, airborne sound through both the interior and exterior layers of the padding.

2. The apparatus according to claim 1, where the at least one board embodies a lossy construction for reducing the acoustical and haptic frequency response in a frequency range of 20 Hz to 1000 Hz.

3. The apparatus according to claim 2, where the lossy construction comprises at least two plates, attached to each other elastically.

4. The apparatus according to claim 2, where the lossy construction comprises at least one perforated board.

5. The apparatus according to claim 1, where the at least one vibrating mechanical actuator comprises at least one of the group consisting of a perforated inertial mass, and a perforated cover.

6. The apparatus according to claim 1, where the at least one board embodies holes or cavities that act as resonators and have length between 5 mm and 100 mm.

7. The apparatus according to claim 1, where an active functional area of the at least one board is extended on edges of the at least one board.

8. The apparatus according to claim 1, where the at least one vibrating mechanical actuator comprises a loudspeaker cone element that is connected mechanically to the at least one board.

9. The apparatus according to claim 1, wherein the at least one vibrating mechanical actuator causes vibration of the at least one board, the vibration of the at least one board simultaneously emitting having both the first sound part and the second sound part of the sound.

10. A method for providing a listening experience comprising the steps of:
    connecting an audio source to the apparatus in claim 1; and
    using the apparatus to convert a recorded or synthetic audio signal to be perceived through haptic and hearing senses.

* * * * *